United States Patent [19]

Kemp

[11] Patent Number: 5,152,989
[45] Date of Patent: Oct. 6, 1992

[54] BATH ADDITIVE AND ITS USE

[75] Inventor: Helmut Kemp, Grossrosseln, Fed. Rep. of Germany

[73] Assignee: APS Apotheker H. Starke GmbH, Fed. Rep. of Germany

[21] Appl. No.: 612,327

[22] Filed: Nov. 13, 1990

Related U.S. Application Data

[63] Continuation-in-part of Ser. No. 536,213, Jun. 11, 1990, abandoned.

[30] Foreign Application Priority Data

Dec. 8, 1989 [DE] Fed. Rep. of Germany ..... 39407047
Jul. 10, 1990 [EP] European Pat. Off. ........ 90113177.1

[51] Int. Cl.$^5$ .................. A61K 35/78; A61K 7/06; A61K 33/14; A61K 33/04
[52] U.S. Cl. .................. 424/195.1; 424/74; 424/680; 424/709; 514/783; 514/784
[58] Field of Search ............ 424/195.1, 74, 709, 424/880; 514/783, 784, 861, 863, 880

[56] References Cited

U.S. PATENT DOCUMENTS 4,416,808 11/1983 Blaschke et al. .................. 252/547

OTHER PUBLICATIONS

"The Merck Manual," Fifteenth Edition, (1987); pp. 2283-2285.

*Primary Examiner*—John W. Rollins
*Attorney, Agent, or Firm*—Ostrolenk, Faber, Gerb & Soffen

[57] ABSTRACT

A bath additive is proposed which has a base of vegetable or animal raw materials containing an aqueous solution of a mixture of amphoteric, anionic and nonionic substances having a base of a vegetable and/or animal oil and an alcoholic solution having a base of one or more medicinal plants. The bath additive is used as agent for the treatment of microbially-induced as well as chronically endogenous skin diseases.

11 Claims, No Drawings

BATH ADDITIVE AND ITS USE

This is a continuation-in-part of application Ser. No. 07/536,213, filed Jun. 11, 1990, now abandoned.

BACKGROUND OF THE INVENTION

The present invention relates to a bath additive having a base of vegetable and/or animal raw materials, as well as the use of the bath additive for the treatment of skin diseases.

Skin diseases from which a large number of persons suffer can be classified first of all on the basis of their cause into inflammatory skin diseases caused by bacteria, protozoa, viruses, parasites or fungi, for instance syphilis, shingles, scabies, allergic and autoimmune-induced skin diseases, for example endogenic eczema, and skin diseases of unknown cause, for instance psoriasis. As a rule, antimicrobial ointments are used for mycotic, bacterial and viral skin diseases, they, however, having a skin-irritating action and possibly so negatively affecting the acid covering of the skin that a new attack by fungi and bacteria takes place. For the treatment of psoriasis, cortisone-containing ointments or a combined treatment consisting of a photosensitizer, for instance a retinoid, followed by UVA-radiation is generally employed. In this way however, on the one hand, the mineral balance can be disturbed and the skin become flaccid while, on the other hand, very extensive damage to the skin can occur. Treatment with these agents, however, is successful usually only for a short time and is accompanied by very strong side effects.

The increasing doubts as to the use and the, in part, unpredictable side effects of these drugs have led on the part of the persons affected by these skin diseases, as well as on the part of the manufacturer of these drugs, to a search for gentle means having a vegetable or animal base for the treatment of these skin diseases.

From U.S. Pat. No. 4,581,230 there is known a cosmetic composition for the treatment of the hair and skin. The known composition comprises particles of pulverized flowers or flower tops of a definite size in an aqueous medium. Nothing can be derived from that patent that a cosmetic composition should be used for the treatment of microbically-induced as well as chronically endogenous skin diseases.

The object of the present invention therefore is to provide a bath additive having a base of vegetable and/or animal raw materials and the use thereof in medicinal baths by which the consequences of skin diseases can be extensively eliminated, or even completely eliminated, without injurious effects on the skin.

This object is achieved in accordance with the invention by a bath additive having a base of vegetable and/or animal raw materials in accordance with the features set forth in claim 1.

In accordance with one embodiment of the invention, the bath additive contains at least one aqueous solution of a mixture of amphoteric, anionic and/or nonionic substances (surfactant mixture) having a base of vegetable and/or animal fats and oils and an alcoholic solution having a base of one or more medicinal plants. By aqueous solution as used in this invention, there is understood the mixture of dissolved surfactants or surfactants present in solution and added water. As vegetable and/or animal fats and oils, use may be made in accordance with the invention of those obtained from sebaceous glands of sheep, coconut, castor oil plant, soya bean or the like. By the use of these solutions in the bath additive, both an antibiotic action and a mitigating of inflammatory processes is possible. Due to the absence of injurious chemical substances, for instance cortisones, no accompanying phenomena which have a negative action on the skin or the mineral balance occur.

The bath additive of the present invention obtained from the raw materials contains 85 to 95% by weight of the aqueous solution having a base of vegetable and/or animal oils and fats, 5 to 15% by weight of the alcoholic solution having a base of medicinal plants, and up to 1.5% by weight and preferably 0.5 to 1.3% by weight of inorganic salts. With this composition, the skin-friendly action of the medicinal plants as well as the desired adjustment of the viscosity and the adjustment of the pH in the neutral to slightly acid range which is favorable for the skin add to the synergistic effect of the surface-active substances.

The inorganic salt used as thickener or viscosity-regulator is preferably sodium chloride and the pH of a 1% solution of the bath additive is 6.5–7.5, and preferably 7.3.

It has been found advantageous for the aqueous solution to contain solids in an amount of 18 to 24% by weight, 4 to 8% by weight of a solvent or solubilizer, as well as 70 to 75% by weight of water, referred to the total weight of the aqueous solution. As the solvent which prevents the solids from flocculating out in water a lower alcohol is used, preferably ethanol or isopropyl alcohol of a purity of at least 90% by volume, the medical doubts inherent in other organic solvents being thus excluded. It has been found in this connection that with a composition of the aqueous solution lying within the range of the invention, the action on the affected regions of the skin is greatest.

In order to achieve the intended effect, the solids of the aqueous solution having a base of a vegetable and/or animal fat or oil can contain 2 to 3% by weight and preferably 2.5% by weight of amphoteric substances, 11.1 to 12.5% by weight, and preferably 12.0% by weight of anionic substances, and 4.8 to 5.9% by weight, and preferably 5.5% by weight, of nonionic substances. With this composition, as well as a content of 73% by weight water and 5% by weight of solubilizer, the aqueous solution of the bath additive of the invention is particularly advantageous.

In accordance with another embodiment of the invention, the bath additive contains 91 to 97% by weight of the aqueous solution having a base of the vegetable and/or animal fat and oil, 0.01 to 8% by weight of the alcoholic solution having a base of the medicinal plants, and up to 4% by weight and preferably 2.7 to 3.8% by weight, of inorganic salts. The same vegetable and/or animal fats and oils as in the first embodiment are used, the bath additive exhibiting substantially the same action. The inorganic salt used as thickener or viscosity regulator is preferably sodium chloride and the pH of a 1% solution of the bath additive is from 6.8 to 7.4.

The aqueous solution of the bath additive in accordance with the above embodiment contains 3 to 7% by weight and preferably 4.8 to 6.5% by weight, of amphoteric substances, 40 to 55% by weight, and preferably 43 to 49% by weight, of anionic substances, 1 to 8% by weight, and preferably 3.8 to 6.5% by weight, of nonionic substances, 30 to 40% by weight, and preferably 33.5 to 38.5% by weight, of water, as well as 1 to 5% by weight and preferably 2.5 to 4.2% by weight, of a solvent or solubilizer, the percentages by weight referring to the total weight of the bath additive. The solubilizer, which prevents the flocculating of the surfactants in the water is, as in the case of the first embodiment of the invention, a lower alcohol, preferably ethanol or isopropyl alcohol of a purity of at least 90% by volume.

In accordance with the invention, an aminocarboxylate or an amino compound of betaine structure is used as amphoteric substance, a salt of an alkylpolyglycolethersulfate as anionic substance, and a fatty alcohol polyglycolether as nonionic substance, the amphoteric, anionic and nonionic substances having a base of coconut oil. These substances are obtained in known manner from the coconut fatty acids contained in the seeds of the coconut palm and suitably converted, and are substantially physiologically and medicinally unobjectionable in the above-indicated amount.

The amphoteric substance obtained from coconut oil is, in accordance with the invention, an alkyl-substituted ammonium betaine, a dicarboxyldiamine of betaine structure, or a fatty acid amide derivative of betaine structure, the anionic substance is the sodium salt of sulfated C12 to C14 fatty alcohols of an ethoxylation number (EO number) of 2 to 3, and a C12 to C14 fatty alcohol polyglycolether of an EO number of 4, 5 or 6. As amphoteric substances mention may be made here of ordinary cocoalkyldimethylammoniumbetaine and laureldimethylcarboxymethylammoniumbetaine and dimethylcarboxymethyl cocofattyacid propylamidoammoniumbetaine (Rewoteric® AM B 13 of the Rewo Company) which, like the commercial anionic and nonionic substances mentioned above, are frequently used in the pharmaceutical and cosmetic industries and are physiologically unobjectionable. Sodium laurylethersulfate (Rewopol® NL 3 of the Rewo Company) as anionic substance and laurylalcoholpolyglycolether (Rewopal® LA 6 of Rewo) as nonionic substance have proven particularly suitable for the invention.

In order to mitigate the inflammatory processes caused by the skin diseases as well as to neutralize the inherent odor possibly present from the raw material of the substances coming from fats or oils, use is made, in accordance with the invention of plant extracts obtained in known manner by glycol extraction from yarrow, oat straw and/or camomile, the disinfecting, pain-alleviating and detumescent action of their active substances, for instance essential oils, alkaloids, amino acids and glycocides, being known from phytotherapy. The use of yarrow, oat straw and camomile extracts in an amount of 2 to 8% by weight of each extract, referred to the total weight of the bath additive, in accordance with the first embodiment or in an amount of 0.01 to 8% by weight of each extract, referred to the total weight of the bath additive in accordance with the second embodiment is advantageous for the present invention, the amount depending essentially on the concentration of the medicinal-plant extract in the alcoholic solution in the two embodiments. The use of a vegetable oil instead of an alcoholic solution of the vegetable extracts of course also falls within the scope of the present invention.

The bath additive having a base of vegetable and/or animal raw materials in accordance with the present invention is used as agent for the treatment of microbially caused as well as chronically endogenous skin diseases, and preferably for the treatment of psoriasis, in medicinal baths. The bath additive can be used by itself or as support for the medical treatment of skin diseases.

A mixture of 90.98% by weight of the aqueous solution and 10% by weight of the medicinal plant extracts according to the first embodiment which is used in a ratio of bath additive to water of 1:400 to 1:1000 or of about 97 to 99.98% by weight of a solution consisting of about 96 to 98% by weight of aqueous solution and about 1 to 4% by weight of inorganic salts, as well as 0.02 to 3% by weight of medicinal-plant extract in accordance with the second embodiment, which is used in a ratio of bath additive to water of 1:250 to 1:800, has proven particularly promising. Repeated sitting or lying for 25 to 30 minutes in the aforementioned bath water leads to success in 90 to 95% of all cases of psoriasis.

The invention will be described in further detail below with reference to an example.

A first solution of a commercially available camomile extract in the amount indicated in the following table, together with a partial amount of laurylalcoholpolyglycolether (EO No. 6) in ratio of camomile extract to laurylalcoholpolyglycolether of 1:50 to 1:100, is first of all prepared in a container of suitable size and stirred for five to ten minutes. Thereupon the sodium chloride required for the adjustment of the viscosity is completely dissolved in either water which has been freed of microbial impurities ("purified water") or tap water of a temperature of 60° to 80° C. in the amounts indicated in the Table in order to prepare a second solution. The first solution, the remaining amount of laurylalcoholpolyglycolether, the amounts of isopropyl alcohol, commercially available dimethyl-carboxymethylcocofatty-acid propylamidoammoniumbetaine, as well as sodium laurylethersulfate (EO No. 3) indicated in the Table and the second solution are then introduced, one after the other, into a third container and stirred with a turbo agitator or the like with a power of 2 KW for about ten minutes. The solution obtained in this way is then set aside for 18 to 24 hours and then again mixed thoroughly for five minutes with the turbo agitator and packed after the bath additive of the invention is completely free of foam.

TABLE

| | |
|---|---|
| Camomile extract | 0.03 g |
| Laurylalcoholpolyglycolether (Rewopal ® LA 6) | 5.50 g |
| Isopropylalcohol | 3.00 g |
| Dimethylcarboxymethylcocofattyacid-propylamidoammoniumbetaine, (Rewoteric ® AM B 13) | 6.00 g |
| Sodiumlaurylethersulfate (Rewopol ® NL 3) | 45.00 g |
| NaCl | 3.5 g |
| Water (purified water") | 36.97 g |

What is claimed is:

1. A bath additive for the treatment of psoriasis comprising:
85 to 95 percent by weight of an aqueous solution comprising a mixture of
amphoteric compounds selected from the group consisting of coco-alkyldimethylammoniumbetaine, lauryldimethylcarboxymethylammoniumbetaine and dimethylcarboxymethyl cocofatty-acid propylaminoammoniumbetaine,
anionic compounds selected from the group consisting of sodium salts of sulfated $C_{12}$ to $C_{16}$ fatty alcohols of an ethoxylation number of 2 to 3, and
non-ionic compounds selected from the group consisting of $C_{12}$ to $C_{14}$ fatty alcohol polyglycolethers of an ethoxylation number of 4 to 6, said aqueous solution having a base of coconut oil;
  5 to 15 percent by weight of a solution comprising
    4 to 8 percent by weight of at least one pharmaceutically acceptable alcohol selected from the group consisting of ethanol and isopropyl alcohol, and
    2 to 8 percent by weight of a plant extract selected from the group consisting of yarrow, oat straw, chamomile and mixtures thereof; and
  up to 1.5 percent by weight of sodium chloride as a viscosity regulator.

2. A bath additive according to claim 1, comprising preferably from 0.5 to 1.3 percent by weight of sodium chloride as a viscosity regulator.

3. The bath additive according to claim 1, wherein said aqueous solution comprises from 3 to 7% by weight of said amphoteric compounds, 40 to 55% by weight of said anionic compounds, 1 to 8% by weight of said nonionic compounds, 30 to 40% by weight of water, and 1 to 5% by weight of a lower alcohol, as referred to the total weight of the bath additive.

4. A method of treating microbially induced and chronically endogeneous skin diseases, comprising administering to a patient in need thereof the composition of claim 1.

5. A bath additive for the treatment of psoriasis comprising:
  85 to 95 percent by weight of an aqueous solution comprising a mixture of
    amphoteric compounds selected from the group consisting of coco-alkyldimethylammoniumbetaine, lauryldimethylcarboxymethylammoniumbetaine, dimethylcarboxymethyl cocofatty-acid propylaminoammoniumbetaine,
    anionic compounds selected from the group consisting of sodium salts of sulfated $C_{12}$ to $C_{16}$ fatty alcohols of an ethoxylation number of 2 to 3, and
    non-ionic compounds selected from the group consisting of $C_{12}$ to $C_{14}$ fatty alcohol polyglycolethers of an ethoxylation number of 4 to 6,
  said aqueous solution compounds having a base of coconut oil;
  5 to 15 percent by weight of a solution comprising
    a vegetable oil solution of a plant extract selected from the group consisting of yarrow, oat straw, chamomile and mixtures thereof; and
  up to 1.5 percent by weight of sodium chloride as a viscosity regulator.

6. A bath additive for the treatment of psoriasis comprising:
  85 to 95 percent by weight of an aqueous solution comprising a mixture of
    amphoteric compounds selected from the group consisting of coco-alkyldimethylammoniumbetaine, lauryldimethylcarboxymethylammoniumbetaine, and dimethylcarboxymethyl cocofatty-acid propylaminoammoniumbetaine,
    anionic compounds selected from the group consisting of sodium salts of sulfated $C_{12}$ to $C_{16}$ fatty alcohols of an ethoxylation number of 2 to 3, and
    non-ionic compounds selected from the group consisting of $C_{12}$ to $C_{14}$ fatty alcohol polyglycolethers of an ethoxylation number of 4 to 6,
  said aqueous solution having a base selected from the group consisting of plant fats, plant oils, animal fats, animal oils and mixtures thereof;
  5 to 15 percent by weight of a solution comprising
    4 to 8 percent by weight of at least one pharmaceutically acceptable alcohol selected from the group consisting of ethanol and isopropyl alcohol and
    2 to 8 percent by weight of a plant extract selected from the group consisting of yarrow, oat straw, chamomile and mixtures thereof; and
  up to 1.5 percent by weight of sodium chloride as a viscosity regulator.

7. A bath additive for the treatment of psoriasis comprising:
  91 to 97 percent by weight of an aqueous solution comprising a mixture of
    amphoteric compounds selected from the group consisting of coco-alkyldimethylammoniumbetaine, lauryldimethylcarboxymethylammoniumbetaine and dimethylcarboxymethyl cocofatty-acid propylaminoammoniumbetaine,
    anionic compounds selected from the group consisting of sodium salts of sulfated $C_{12}$ to $C_{16}$ fatty alcohols of an ethoxylation number of 2 to 3, and
    non-ionic compounds selected from the group consisting of $C_{12}$ to $C_{14}$ fatty alcohol polyglycolethers of an ethoxylation number of 4 to 6,
  said aqueous solution having a base of coconut oil;
  0.01 to 8 percent by weight of a solution comprising
    at least one pharmaceutically acceptable alcohol selected from the group consisting of ethanol and isopropyl alcohol, and
    a plant extract selected from the group consisting of yarrow, oat straw, chamomile and mixtures thereof; and
  up to 4 percent by weight of sodium chloride as a viscosity regulator.

8. A bath additive according to claim 7, comprising preferably from 2.7 to 3.8 percent by weight of sodium chloride as a viscosity regulator.

9. The bath additive according to claim 7, wherein said aqueous solution comprises from 3 to 7% by weight of amphoteric compounds, 40 to 55% by weight of anionic compounds, 1 to 8% by weight of nonionic compounds, 30 to 40% by weight of water, and 1 to 5% by weight of a lower alcohol, as referred to the total weight of the bath additive.

10. A method for the treatment of skin diseases by immersing the affected portion of skin in bath water containing a bath additive comprising:
  85 to 95 percent by weight of an aqueous solution comprising a mixture of
    amphoteric compounds selected from the group consisting of coco-alkyldimethylammoniumbetaine, lauryldimethylcarboxymethylammoniumbetaine, and dimethylcarboxymethyl cocofatty-acid propylaminoammoniumbetaine;
    anionic compounds selected from the group consisting of sodium salts of sulfated $C_{12}$ to $C_{16}$ fatty alcohols of an ethoxylation number of 2 to 3, and
    non-ionic compounds selected from the group consisting of $C_{12}$ to $C_{14}$ fatty alcohol polyglycolethers of an ethoxylation number of 4 to 6,
  said aqueous solution having a base selected from the group consisting of plant fats, plant oils, animal fats, animal oils and mixtures thereof;
  5 to 15 percent by weight of a solution comprising
    4 to 8 percent by weight of at least one pharmaceutically acceptable alcohol selected from the group consisting of ethanol and isopropyl alcohol and 2 to 8 percent by weight of a plant extract selected from the group consisting of yarrow, oat straw, chamomile and mixtures thereof; and up to 1.5 percent by weight of sodium chloride as a viscosity regulator.

11. A method according to claim 10, wherein the said skin disease is selected from the group consisting of neurodermatitis, seborrheic eczema or psoriasis.

* * * * *